United States Patent
Woodburn

(10) Patent No.: US 11,273,320 B2
(45) Date of Patent: *Mar. 15, 2022

(54) DEVICE FOR PHOTO-THERAPY OF GROVER'S DISEASE AND USE THEREOF

(71) Applicant: Tcellerate LLC, Stamford, CT (US)

(72) Inventor: William Woodburn, Greenwich, CT (US)

(73) Assignee: TCELLERATE LLC, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/168,768

(22) Filed: Oct. 23, 2018

(65) Prior Publication Data

US 2019/0054310 A1    Feb. 21, 2019

Related U.S. Application Data

(63) Continuation-in-part of application No. 15/608,588, filed on May 30, 2017, now Pat. No. 10,155,122.

(51) Int. Cl.
*A61N 5/06* (2006.01)

(52) U.S. Cl.
CPC ...... *A61N 5/0616* (2013.01); *A61N 2005/064* (2013.01); *A61N 2005/0626* (2013.01); *A61N 2005/0633* (2013.01); *A61N 2005/0639* (2013.01); *A61N 2005/0643* (2013.01); *A61N 2005/0651* (2013.01); *A61N 2005/0661* (2013.01); *A61N 2005/0662* (2013.01)

(58) Field of Classification Search
CPC .............................. A61N 5/0616; A61N 5/0614
See application file for complete search history.

(56) References Cited

U.S. PATENT DOCUMENTS

| | | | |
|---|---|---|---|
| 3,986,513 A | 10/1976 | Stuhl | |
| 4,309,616 A * | 1/1982 | Wolff | A61N 5/0614 250/494.1 |
| 4,444,189 A | 4/1984 | Seiverd | |
| 6,269,818 B1 * | 8/2001 | Lui | A61K 49/0017 128/898 |
| 6,896,693 B2 | 5/2005 | Sullivan | |

(Continued)

FOREIGN PATENT DOCUMENTS

EP   2 044 973 A1   4/2009

OTHER PUBLICATIONS

Breuckmann, "Medium-dose ultraviolet A1 phototherapy in transient acantholytic dermatosis (Grover's disease)," J. Am. Acad. Dermatol., 52(1):169-170 (Jan. 2005).

(Continued)

*Primary Examiner* — Gary Jackson
*Assistant Examiner* — Zahed Kabir
(74) *Attorney, Agent, or Firm* — Fox Rothschild LLP

(57) ABSTRACT

The present invention provides a photo-therapy device and its use for treatment of skin conditions such as rashes or similar dermatological conditions that are exhibited by Grover's disease or other diseases which are associated or co-existent with Grover's disease. The treatment includes exposure of the subject's affected skin and preferably the entire body with blue LED light to improve skin status by stimulating body's immune system to reduce itching, blotchiness and skin discomfort.

11 Claims, 7 Drawing Sheets

(56) References Cited

U.S. PATENT DOCUMENTS

| | | | |
|---|---|---|---|
| 7,066,941 B2 | 6/2006 | Perricone | |
| 9,463,333 B2 | 10/2016 | Wagenaar Cacciola et al. | |
| 2002/0029071 A1 | 3/2002 | Whitehurst | |
| 2002/0145859 A1* | 10/2002 | Chubb | A41D 7/006 362/1 |
| 2002/0198575 A1 | 12/2002 | Sullivan | |
| 2004/0093043 A1 | 5/2004 | Edel et al. | |
| 2005/0093485 A1* | 5/2005 | Spivak | A61N 5/0614 315/291 |
| 2006/0293727 A1 | 12/2006 | Spooner et al. | |
| 2008/0065056 A1 | 3/2008 | Powell et al. | |
| 2008/0125834 A1 | 5/2008 | Hendrix et al. | |
| 2009/0005838 A1* | 1/2009 | Wagenaar-Cacciola | A61N 5/0614 607/91 |
| 2009/0247932 A1 | 10/2009 | Barolet | |
| 2010/0063487 A1 | 3/2010 | Van Straalen | |
| 2010/0069898 A1* | 3/2010 | O'Neil | A61B 18/203 606/9 |
| 2010/0179622 A1 | 7/2010 | Wagenaar Cacciola et al. | |
| 2012/0101557 A1 | 4/2012 | Wagenaar Cacciola et al. | |
| 2012/0310307 A1 | 12/2012 | Zhou | |
| 2015/0112411 A1 | 4/2015 | Beckman et al. | |
| 2016/0008623 A1 | 1/2016 | Jones et al. | |
| 2016/0101294 A1 | 4/2016 | Sun et al. | |
| 2016/0175608 A1 | 6/2016 | Livingston | |
| 2016/0175609 A1 | 6/2016 | Dye et al. | |
| 2016/0331993 A1 | 11/2016 | Moyer | |
| 2017/0080246 A1 | 3/2017 | Knight | |
| 2017/0216616 A1 | 8/2017 | Boyajian et al. | |

OTHER PUBLICATIONS

Liebmann et al., "Blue-Light Irradiation Regulates Proliferation and Differentiation in Human Skin Cells," Journal of Investigative Dermatology, 130:259-269 (Jan. 2010).

Phan et al., "Intrinsic Photosensitivity Enhances Motility of T Lymphocytes," Scientific Reports, 6:39479 (11 pgs.) (Dec. 2016).

Weaver et al., "Grover Disease (Transient Acantholytic Dermatosis)," Arch Pathol Lab Med, 133:1490-1494 (Sep. 2009).

Skin Disorders in Older Adults: Papulosquamos and Bullous Diseases, Part 1. Published in: Consultant, vol. 51, issue 3, dated Mar. 2011.

U.S. Appl. No. 15/608,588, Restriction Requirement, dated Aug. 31, 2017.

U.S. Appl. No. 15/608,588, Non-Final Rejection, dated Feb. 8, 2018.

U.S. Appl. No. 15/608,588, Final Rejection, dated Jun. 29, 2018.

U.S. Appl. No. 15/608,588, Notice of Allowance, dated Sep. 25, 2018.

* cited by examiner

DEVICE FOR PHOTO-THERAPY OF GROVER'S DISEASE AND USE THEREOF

CROSS-REFERENCE TO RELATED APPLICATIONS

This application is a continuation-in-part of application Ser. No. 15/608,588 filed May 30, 2017, the entire content of which is expressly incorporated herein by reference thereto.

FIELD OF THE INVENTION

The present invention provides a photo-therapy device for treatment of skin conditions such as rashes or similar dermatological conditions that are exhibited by Grover's disease or other diseases which are associated or co-existent with Grover's disease.

BACKGROUND OF THE INVENTION

Grover's disease, also known as transient acantholytic dermatosis, is a transient skin disorder that consists of papulovesicular rash, such as small raised red lesions, on the skin of the chest and back. The rash can be a sudden onset of small papules and fragile vesicles with the formation of crusts and keratotic erosions (Weaver et al., Grover disease (transient acantholytic dermatosis), Arch Pathol Lab Med. 2009 September; 133 (9):1490-4). It is a skin disorder seen mainly in males over the age of forty, and particularly among older white males.

The rash from Grover's disease can be extraordinarily itchy with the presence of small blisters containing a watery liquid. The itching may be severe and difficult to treat in some patients. The steroid creams (such as triamcinolone or clobetasol), antihistamines (such as diphenhydramine or hydroxyzine), tetracycline, or oral retinoids (such as acetretin, or isotretinoin) may provide temporary relief of the itching and inflammation. The evaluation of treatment of Grover's disease is difficult due to its spontaneous remittance and occasional fluctuant course with unknown pathogenesis.

In some conditions, photo-therapy may be effective to treat Grover's disease, including exposing the skin to controlled amounts of natural sunlight, ultraviolet A light (UVA, wavelength of 315-400 nm), or ultraviolet B light (UVB, wavelength of 280-315 nm). Unfortunately, exposure to light can sometimes intensify Grover's disease. Medium-dose UVA cold-light mono-photo-therapy containing a special filtering and cooling system has been tested for administration to treat Grover's disease. It did result in some improved skin status and was well-tolerated without the occurrence of acute side-effects. (Breuckmann et al., Medium-dose ultraviolet A1 phototherapy in transient acantholytic dermatosis (Grover's disease), J. Am Acad Dermatol, January 2005, vol 52, no 1, pages 169-170).

Various devices have been designed to provide photo-therapy for a variety of skin treatments or tanning. U.S. Pat. No. 6,896,693 (Sullivan, Photo-therapy Device) discloses a photo-therapy device containing arrays of light-emitting diodes (LED) allowing the therapeutic treatment to take place at a more comfortable distance from the patient's skin surface, including whole body treatment. U.S. Pat. No. 7,066,941 (Perricone, Apparatus for skin treatment) discloses a system comprising an array of LEDs having a wavelength of about 400-500 nm for treating aging or damaged skin. US 2012/0101557 A1 (Wagenaar Cacciola et al., Treatment apparatus and use thereof for treating psoriasis) discloses an apparatus comprising a radiation source emitting radiation and a radiator for guiding the emitted radiation to the parts of the skin which is affected by psoriasis. EP 2044943 A1 discloses a photo-therapy device comprising a matrix board with LED (red light and blue light wavelength) and a control system board for preventive treatment, rehabilitation and the treatment of many diseases. US 2008/0065056 A1 (Powell et al., Skin treatment photo-therapy method) discloses a photo-therapy device with the design of a clamshell structure, pen shape, facial mask, or desk lamp comprising multi-color LEDs for emitting multiple wavelengths of light for treating skin conditions, including acne, wrinkle, rosacea, sun spots, inflammation, lesions, or skin blemishes. U.S. Pat. No. 9,463,333 B2 (Wagenaar Cacciola et al., Skin treatment device, lamp and use) discloses a device comprising lamps emitting UV-light and blue light (400-440 nm) for tanning and anti-acne.

US patent application no. 2006/0293727 A1 discloses a system and method comprising a plurality of light emitting diodes for treating an exposed tissue of a patient with a light energy, wherein the light emitting diodes are disposed over an area of a supporting structure. US 2006/0293727 A1 does not disclose the use of blue LED light but instead discloses the use of light energy comprising a substantial band of wavelengths between about 380 and 800 nm which wavelengths cover the full spectrum of visible light. US 2006/0293727 A1 discloses an LED fixture and detailed design parameters for treating acne using low power, broader range of light wavelengths to fluoresce small, specific skin surface areas. Fluoresce requires utilizing light on a specific tissue area to fluoresce active bacterial molecules of the exposed the tissue, meaning to give off electrons in the tissue cells which causes the cells to die.

While the prior art photo-therapy devices have some utility, there is no effective treatment for Grover's disease, skin rashes and other dermatological conditions. The present invention now provides a photo-therapy device and use thereof that solves a need in the art for a successful treatment of such conditions.

SUMMARY OF THE INVENTION

The present invention provides a photo-therapy device for applying blue LED light upon a subject in need of absorbing radiation of such light. The photo-therapy device comprising a plurality of lamps each having a wattage of at least 5 W, e.g., between 5 W and 100 W, that generate blue LED light, the lamps being configured and arranged on one or more supporting surfaces to provide a uniform application of the radiation at a total exposure time of at least 10 minutes, with the emitted blue light having a wavelength in the range of between 410 and 490 nm.

In this configuration and arrangement of the plurality of lamps on the one or more supporting surfaces a uniform application of the radiation onto exposed skin surfaces of the subject is provided so that the subject absorbs at least 250 to as much as 3000 watt-minutes or more of such radiation.

A method of treating a skin rash is also described. This method comprises applying blue LED light radiation to exposed skin surfaces of a subject in need of such treatment at a sufficient energy and for a sufficient time so that the subject typically absorbs between 500 and 3000 watt-minutes of such radiation to treat, reduce or eliminate the rash is also described. There is no upper limit on the time of treatment or the amount of absorption except as to practical limits on the actual time that a patient must spend for treatment. Generally, this would not be more than about 100 minutes and in particular a treatment time that is 1 hour or less is more than sufficient. Typically, treatment times are between 10 to 60 minutes are effective. Treatments can be conducted daily, 2, 3 or 4 times per week or even weekly depending upon the extent of the rash. Longer or multiple treatment times lead to greater amounts of absorption and greater T-cell activation which also affects how fast the rash can be resolved or minimized. This can vary based on the patient and extent of the rash.

The rash is typically present on the subject from Grover's disease or other diseases which are associated or co-existent with Grover's disease and the photo-therapy device of the present invention is particularly useful for treatment of skin conditions such as rashes or similar dermatological conditions that are exhibited by Grover's disease or other diseases which are associated or co-existent with Grover's disease.

Exposing a patient for 10 minutes on his or her front side followed by 10 minutes on his or her back side with blue LED light from lamps having a wattage of, e.g., 35 W, and repeating this treatment for three times a week increases T-cell activation significantly to reduce the rash.

Also, a preferred patient population is where the subject to be treated is a male who is 40 years old or older. Preferably, the subject absorbs at least between 600 to as much as 2500 watts-minute or more, with at least 1200 watts-minute of the radiation being suitable. Again, there is no upper limit of absorption expect as practical limits on time of treatment. As a patient would likely go to a physician's office or photo therapy center for treatment, times of between 30 to 40 minutes are convenient although if additional absorption is needed, an additional time per treatment or additional or multiple treatments can be conducted. Also, differing times of exposure can be used for certain rash conditions depending upon how the rash responds to such treatments.

The radiation is uniformly applied to the exposed skin surfaces of the subject by a plurality of blue LED light generating lamps having a wattage of between 5 W and 100 W with the emitted blue light having a wavelength in the range of between 410 and 490 nm, between 425 and 475 nm or at about 450 nm. These lamps preferably each have a wattage of about 25 to 60 watts, preferably about 35 to 50 watts, and the subject undergoes one or more treatments at a total exposure time of between 10 and 100 minutes for each treatment of the subject. For this, the lamps are placed about 5.08 cm to 50.8 cm, 7.62 cm to 50.8 cm, or 10.16 cm to 25.4 cm (2 to 20, 3 to 12, or 4 to 10 inches) away from the subject's skin.

There is no required upper limit on the time of treatment or the maximum wattage of the LED lamps except those imposed by practical conditions, such as the ability of the patient to be available for long time treatments or the availability of higher wattage lamps that are commercially or otherwise available.

The radiation may be provided by a plurality of blue LED light generating baton lamps affixed to one or more surfaces, with the lamps arranged in a pattern to emit substantially uniform radiation upon the subject. The baton lamps are generally provided on a flat surface that is placed above, in front of or in back of the subject. The lamps also may be arranged in a vertical chamber in which the subject can stand to apply the radiation to all exposed skin surfaces at one time. Each baton can be provided on a separate support surface if desired. Also, the method further comprises configuring the one or more surfaces to be movable for positioning such surface(s) near the subject for treatment.

The invention thus relates to a photo-therapy device for applying blue LED light upon a subject in need of absorbing radiation of such light. The photo-therapy device comprises a plurality of lamps having a wattage of between 5 W and 100 W or more that generate blue LED light, the lamps configured and arranged on one or more supporting surfaces to provide a uniform application of the radiation onto exposed skin surfaces of the subject so that the subject absorbs at least 250 to 3000 watt-min of such radiation.

The lamps have a wattage of about 25 to 60 watts, preferably about 35 to 50 watts. Higher wattage lamps which are available up to around 200 watts can be used if desired. As noted, the commercial availability of high wattage lamps may be considered, but lower wattage lamps of the values mentioned herein are entirely acceptable. Higher wattage lamps generally require shorter treatment times. One can determine the optimum combination of wattage and treatment time based on the preferred values disclosed herein.

The lamps also have a wavelength that is limited to the range of between 410 and 490 nm, preferably between 425 and 475 nm or most preferably at about 450 nm. Also, the one or more support surface(s) may be a wall with the subject standing adjacent the wall at a distance corresponding to the desired absorption or radiation based on a selected treatment time. In this embodiment, the lamps are arranged on the wall to allow the subject to stand adjacent the wall with one side of his or her body facing the lamps for a first period of treatment for that side and then to turn to orient his or her opposite side to face the lamps for a further period of treatment. The subject may initially stand with his or her chest facing the lamps for one treatment and also orients his or her back facing the lamps for another treatment. These treatments can occur in any order.

In another embodiment, the one or more support surface(s) comprise(s) one or more structure(s) associated with and placed above an upper surface of a bed or table, so that the subject can lie on the upper surface of the bed or table with one side of his or her body facing the lamps for a first period of treatment on that side and then to turn to orient his or her opposite side to face the lamps for a further period of treatment. For example, the subject can lie on the bed or table surface with his or her chest facing the lamps for treatment of their front side, and then the subject lies on his or her stomach on the table with their back facing the lamps for treatment of their backs. Preferably, the one or more structure(s) is/are pivotably associated with a wall or upright member that allows the structure(s) to be pivoted out of the way to allow the subject to lie on the table and then to be pivoted toward the subject to an appropriate distance above the subject for conducting the radiation treatments.

In a preferred arrangement, the photo-therapy device includes between 2 and 12, between 2 and 8, or between 2 and 4 baton lamps oriented longitudinally along the height of the subject with at least two baton lamps aligned with the subject's upper torso and optionally but preferably with at least two additional baton lamps aligned with the subject's legs. Each lamp preferably has a wattage in the range of between 5 and 100 watts or more as described while typical wattages are between 25 and 50 watts. The lamps are arranged about 5.08 cm to 50.8 cm, or 7.62 cm to 50.8 cm, or 10.16 cm to 25.4 cm (about 2 to 20, about 3 to 12 or about 4 to 10 inches) from the subject's skin. Lamps with these preferred wattages if not commercially available, can certainly be designed and configured by skilled artisans in the field of blue LED light generation.

In the present invention, the term "substantially uniform radiation" is used to mean radiation of an amount and direction such that all portions of the exposed skin of the subject's body are exposed with radiation at a distance that provides an intensity to meet the minimum requirements for treatment. It is recognized that the radiation can be applied from blue LED light emitting lamps arranged to uniformly radiate one side (i.e., the front) of the subject while the subject is lying on a bed or table, before the subject can turn over so that his or her back side can be exposed to the radiation (or vice versa). In other embodiments, a vertical surface with such lamps can be provided for sequential front and back (or back and then front) exposure, or a round or pentagonal chamber can be provided with lamps that are arranged to provide simultaneous radiation around and surrounding the subject.

The present invention provides a photo-therapy device and use thereof for preferably treating Grover's disease and other diseases which are associated or co-existed with Grover's disease. The skin exposure of blue light at appropriate dosages can potentially eliminate or reduce Grover's dermatitis. The present invention provides a photo-therapy device to treat Grover's disease through skin exposure of blue LED light to stimulate the body's immune system to reduce itch, blotchiness and discomfort of skin.

Grover's disease is a transient, self-limiting, and non-immune-mediated skin disorder that consists of papulovesicular rash. The rash is frequently triggered or aggravated by heat, sweating, ultraviolet light exposure, or hospitalization. Grover's disease and other associated dermatitis worsen in winter season. The acantholysis seen in Grover's disease occurs in a variety of different patterns singly or in combination characterized by four different acantholytic histologic patterns, resembling Darier-White disease, pemphigus vulgaris, pemphigus foliaceous, Hailey-Hailey disease, and a spongiotic dermatitis. Grover's disease has been found to be associated with numerous disorders, including hematologic malignancies and occasionally coexisted with other dermatoses including asteatotic eczema, allergic contact dermatitis, atopic dermatitis, irritant contact dermatitis, and psoriasis. (Weaver et al.)

The pathogenesis or the cause of the manifestations of Grover's disease is unknown, but it could relate to the occlusion of damaged eccrine ducts with sweat dispersion in the upper layers of the skin due to its association with sun exposure, heat, sweating, trauma, or sun damaged skin. Grover disease may be considered as a syndrome representing a host inflammatory response to disseminated lesions rather than as a distinct disease. (Weaver et al.) Its nature of spontaneous remittance and occasional fluctuant course with unknown pathogenesis makes the evaluation of treatment difficult and challenging.

Sunlight exposure is both harmful and beneficial to the physiology of human skin. Despites a causative link in skin cancers relevant to ultraviolet (UV) light exposure, sunlight is also associated with positive health outcomes including reduced incidences of autoimmune diseases and cancers. The effects of sunlight in immune function remain unclear. Visible radiation (400-750 nm) penetrates much deeper into the dermis of the skin than UV light.

Human keratinocytes and skin-derived endothelial cells were radiated with LED devices of distinct wavelengths to study the effects on cell physiology. Blue light may be effective in treating hyper-proliferative skin conditions by reducing proliferation by inducing differentiation in human skin-derived keratinocytes. LED radiation with blue light at high fluences, however, can be toxic for endothelial cells and keratinocytes. (Liebmann et al., Blue-light radiation regulates proliferation and differentiation in human skin cells, Journal of Investigative Dermatology, 2010 January; 130 (1):259-69)

Blue LED light of the wavelengths disclosed herein is capable of penetrating several millimeters through skin. Studies have been done to show that the low doses of blue or full spectrum light were not toxic to T lymphocytes, a cell-type highly abundant in skin performing immune surveillance, including memory cells that can be activated in the skin by antigen-presenting cells and other cells actively recruited by inflammation. T lymphocytes had the capacity to sense and respond to light. Blue light stimulated the production of $H_2O_2$ in T lymphocytes in vitro. $H_2O_2$ activated a kinase/phospholipase signaling pathway and $Ca^{2+}$ mobilization. The intrinsic photosensitivity of T lymphocytes may enhance their motility in skin, which may contribute to the effects of sunlight on immune function. (Phan et al., Intrinsic photosensitivity enhances motility of T lymphocytes, Scientific Reports, 2016 Dec. 20; 6:39479).

The blue light exposure that is applied according to the present invention covers the entire exposed surface area of the subject's skin including both the front and back of the subject's body in order to induce massive T cell activation. This is achieved using high output LED blue lights preferably applied to the entire exposed skin surfaces of the subject's body to obtain an effective treatment. The amount of radiation to be absorbed by the subject ranges from at least 250 to as much as 3000 Watts-minute or more, preferably at least 600 Watts-minute and more preferably at least 1200 Watts-minute. The radiation energy that is actually to be absorbed will depend upon the patient's size physiology and degree of rash intensity, but these values have been proven to be optimum for various sized patients. Absorption also depends upon the lamp wattage and time of treatment. The subject to be treated is typically a male patient that is 40 years old or older as that is when the Grover's disease is typically encountered for such subjects. Although there is no upper age limit, such treatments are usually applied to male patients that are between 40 and 90.

Blue LED light radiation is provided for use in treating skin rash on exposed skin surfaces of at least a subject's upper torso including both front and back sides so that the subject absorbs between 250 and 3000 watt-min watts-minute of such radiation, wherein the radiation is uniformly applied to the exposed skin surfaces by a plurality of blue LED light generating lamps each having a wattage of at least 5 W or more and at a total exposure time of at least 10 minutes or more, with the emitted blue light having a wavelength in the range of between 410 and 490 nm. There is no upper limit on the wattage of the lamps except to the extent that such lamps are not available, commercially or otherwise. Blue LED lamps having a wattage of around 175 to 210 W have been made and used and these lamps include a cooling mechanism or heat sink to avoid excessive temperatures. In particular, for initial testing of the invention, two blue LED light sources have been used with each having the following performance factors: 210 Watts, Radiant power of 105 watts at 450 nm wave length. The wave length distribution is tight with 99% at 450 nm. Beam pattern is Lambertain on a 22 inch (0.56 m) long light source emitting surface. The power source or driver is 120 volt input with 240 Volts AC 50/60 Hz. and is self-grounded. Of course, other lamps with lower or higher wattage can be used provided that they generate blue light. The blue LED lamps can be provided as any type of bulb, including Reflector and Par lamp configurations as well as tube lamps or baton lamps provided that it possesses the necessary wattage described herein. Some of these lamps are non-conventional but lamp suppliers such as General Electric are able to prepare custom devices having the necessary performance requirements upon request.

Additional testing of the present invention was conducted using 35-40 watt baton lamps. These LED baton lamps are preferred for use in the photo-therapy devices of the present invention to provide more uniform light coverage and the desired radiation. The LED baton lamp has a typical wattage in the range of about 25 to 60 watts, preferably about 35 to 50 watts, and emits light in wavelength range of from 410 to 490 nm, preferably with the center of the spectrum at 450 nm. The LED baton lamp has the length in the range of about 1.5 to 2.5 feet (0.457 to 0.762 m), preferably in the length of about 58.42 cm (23 inches). The effectiveness of the LED photo-therapy device is enhanced when the LED baton lamps operate in high output levels and are configured to apply the blue light as uniformly as possible. In appearance, they provide blue light in a manner reminiscent of a fluorescent bulb except that the light is blue and stronger in intensity.

The wattage of the lamps is not critical but the larger the wattage, the shorter the time of treatment. While between 5 Watts and 100 Watts are suitable, the exposure times at 5 watts is relatively long while making 100 Watt lamps would be relatively expensive. Accordingly, the wattage in the range of about 25 to 60 watts, preferably about 35 to 50 watts, are the best ranges as these can be made more easily and less expensively while also providing relatively shorter times for the subject to absorb the necessary amount of radiation for successful treatment. As noted herein, single or repeated treatment times of between 30 and 40 minutes at the preferred wattages is generally effective.

The absorption of the radiation can be calculated. First of all, while the total skin area of a person is around 2.1 m$^2$, this include portions of the skin that do not usually receive light, e.g., underarms and armpits, etc. Calculations have been made that demonstrate that the exposed skin area of a subject can vary from about 1.2 to 1.56 m$^2$. For an average application of blue LED light from lamps having a wattage of between 35 and 40 watts applied at a distance of 15.25 cm (6 inches) from the subject's skin (see Table 1), 31.8 watts/m$^2$ are absorbed. Thus, the amount of radiation absorbed by the subject's exposed skin surfaces during three treatments of 16 minutes each would be calculated as follows:

31.8 watts/m$^2$×16 min×3 treatments (for each side)× 1.2 m$^2$=1831.68 watt-min.

For the larger surface area of 1.56 m$^2$, the calculation is:

31.8 watts/m$^2$×16 min×3 treatments (for each side)× 1.56 m$^2$=2381.18 watt-min.

Accordingly, variations in distance, wattage, surface area and the like can vary the absorbed blue light energy over the ranges disclosed in this specification.

Each photo-therapy device may comprise between 2 and 12 but preferably one to four LED baton lamps or two or four LED baton lamps in each device depending upon the type of exposure. The LED baton lamps can be mounted to a wall to minimize the occupied space of the device to minimize the use of tight office space found in most dermatologist offices. The LED baton lamp can be affixed to a movable surface to provide a portable device. Each lamp can be provided upon a separate support that is movable to provide the greatest flexibility of moving the lamps into the best positions for applying the radiation to the subject. For simplicity, the lamps can be provided on a single support that is pivotally mounted on a wall or pillar so that it can be moved away to allow the subject to be placed in the correct position before then being moved toward the subject and at the best distance for providing absorption of the blue light. Therefore, the photo-therapy device of the present invention provides a convenient solution and advantages as a portable or/and compact photo-therapy device which has minimal occupied space or can be in storage or hidden away.

The details of the preferred embodiments of the present invention are set forth in the accompanying figures and detailed description herein. Once these details of the invention are known, numerous additional innovations and changes will become obvious and implementable to one of ordinary skill in the art.

BRIEF DESCRIPTION OF THE FIGURES

Further features of the inventive concept, its nature and various advantages will be more apparent from the following detailed description, taken in conjunction with the accompanying figures:

FIG. 1 is a perspective schematic view of photo-therapy devices according to the invention, wherein FIG. 1A shows a two baton lamp upper torso exposure device while FIG. 1B shows a four baton lamp full body exposure device.

DETAILED DESCRIPTION OF THE INVENTION

Throughout this description, the preferred embodiments and examples provided herein should be considered as exemplar, rather than as limitations of the present invention.

Figures 1A, 1B:
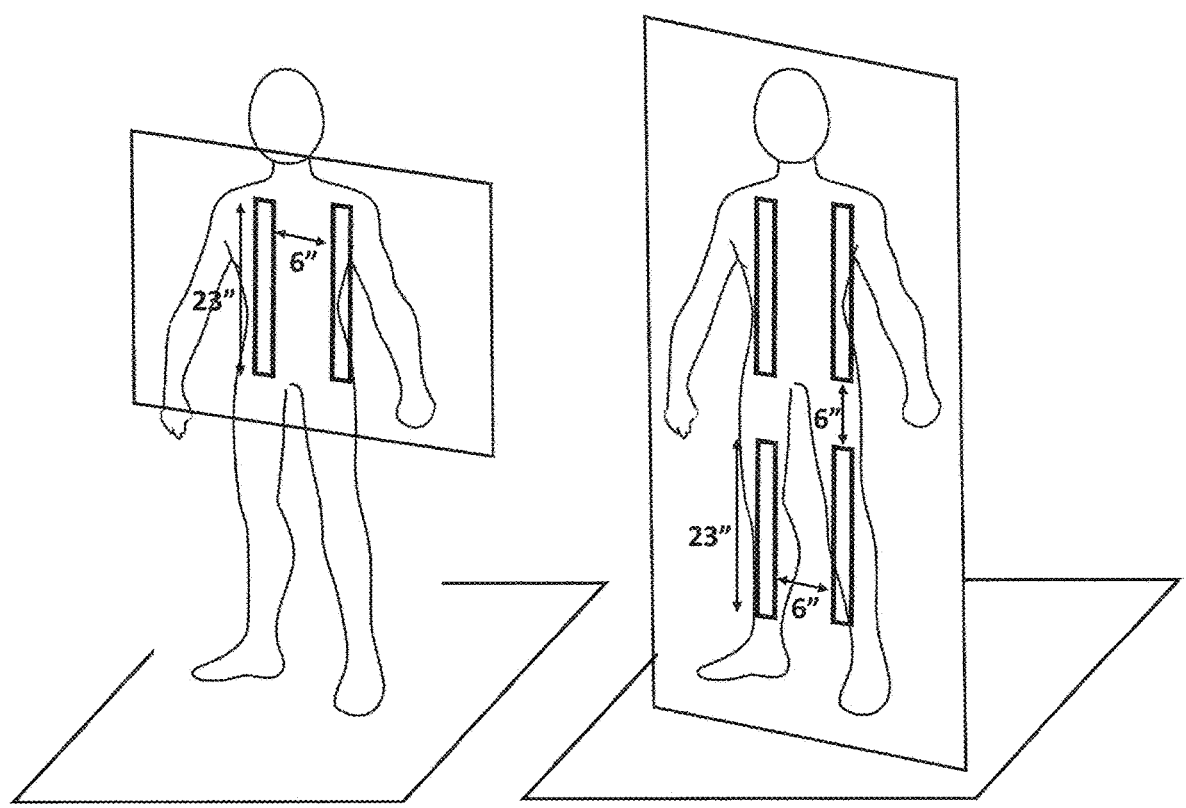

In one embodiment, the photo-therapy device of the present invention comprises four LED baton lamps which are mounted to a wall as shown in FIG. 1B. Preferably, the distance between two vertical lamps in parallel is 15.24 cm (6 inches), and the distance between the upper and lower lamps is 15.24 cm (6 inches) as shown in FIG. 2B. The arrangement in FIG. 1B provides exposure of the entire body one side at a time. When the skin rash occurring from Grover's disease is mostly in the upper trunk of the body, the photo-therapy device of FIG. 1A can be used, as it is smaller and simply comprises two LED baton lamps mounted to a wall or a movable surface to provide a more compact photo-therapy device. The embodiment of the photo-therapy device shown in FIG. 1A provides LED blue light exposure of only the upper trunk or torso of the subject, while in FIG. 1B the exposure is of the patient's full body. The full body exposure is preferred because it provides maximum absorption at a minimum time, but for cases of lesser severity, the upper torso exposure is sufficient. The full body exposure is also preferred because it provides the greatest increase in T cells in the body which would fight the infection.

In an embodiment, a patient stands in front of the light source to expose the front side of the body and then turns around to expose the back side of the body to the light source. The skin of the patient with Grover's disease is exposed to the LED light radiation, but eyes of the patient are protected from the LED lights, such as wearing dark sunglasses with heavy tint or non-transparent material, or by a conventional blindfold that shields the subject's eyes from the light. Additionally, the lamps may be typically mounted on a structure or structures that do not extend above the neck of the patient to minimize the light being directed at the patient's face and eyes.

Figure 2:
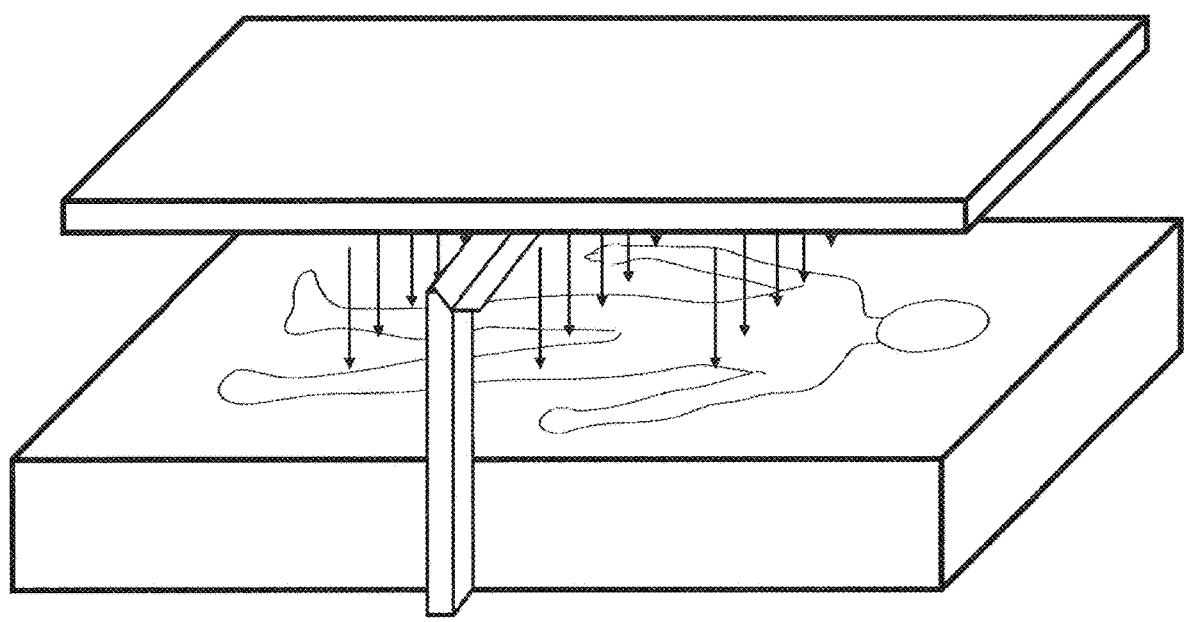
FIG. 2 shows the horizontal operation mode of a photo-therapy device for a patient laying on a bed, wherein a hinge is attached to the long edge of the photo-therapy device.
Figure 3:
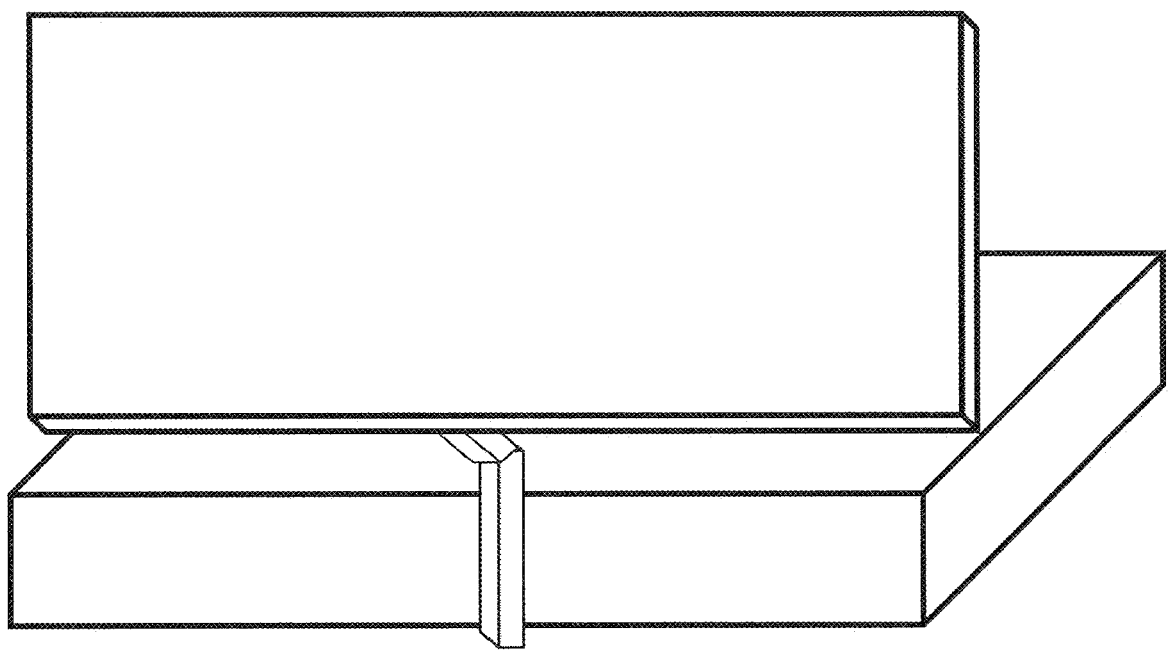
FIG. 3 shows a photo-therapy device in an upright position, wherein a hinge is attached to the long edge of the photo-therapy device.
Figure 4:
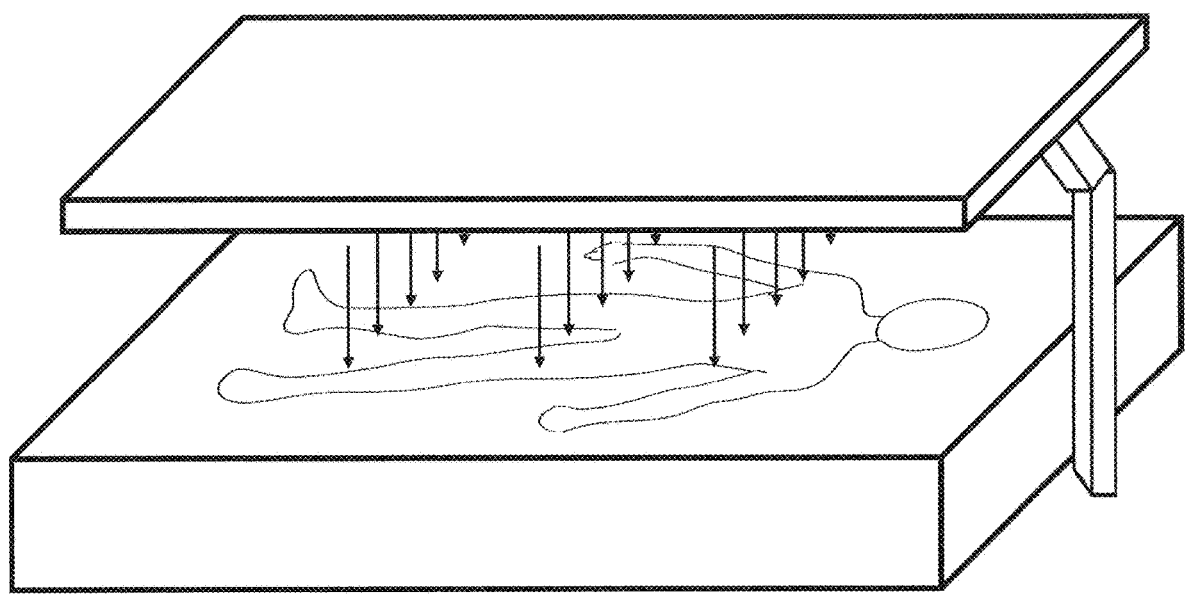
FIG. 4 shows the horizontal operation mode of the photo-therapy device for a patient laying on a bed, wherein a hinge is attached to the short edge of the photo-therapy device.
Figure 5:
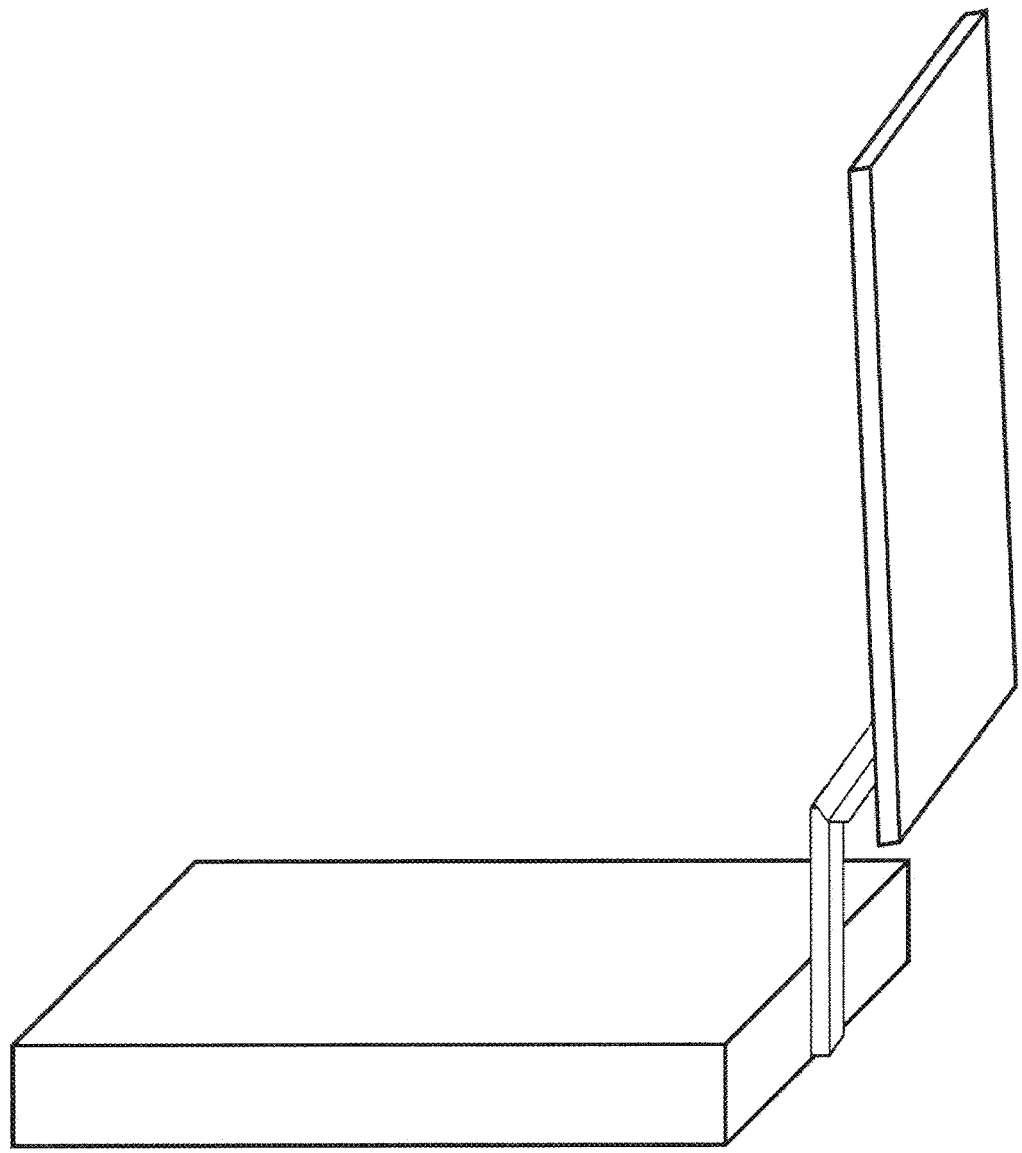
FIG. 5 shows a photo-therapy device in an upright position, wherein a hinge is attached to the short edge of the photo-therapy device.

In another embodiment, the LED baton lamps are affixed to a movable surface, wherein a hinge is attached to the movable surface as shown in FIGS. 2-5. The hinge or pivot point can be attached to the short or long edge of the movable surface depending on the mode of operation or the layout of the doctor's office. The hinge may comprise multiple components to support different positions of the movable surface and may be mounted to a wall or a floor. In one embodiment, a patient lays on a bed, and a photo-therapy device is positioned above the patient's body to provide light exposure as shown in FIGS. 2 and 4. When the photo-therapy device is not in use, it can be positioned in upright position against the wall to minimize the occupied space of the photo-therapy device as shown in FIGS. 3 and 5.

And instead of being mounted on a support, the photo-therapy device can be attached to a wall with a connection that allows the support surface to be pivoted to be adjacent a table or a bed for exposure to the person when the person is lying down.

In yet another embodiment, the lamps can be mounted in a circular or oval chamber which surrounds a standing patient. Part of the chamber acts as a door to allow the subject to step inside before energizing the lamps. Although some subjects may not be comfortable standing in a relatively snug chamber, this embodiment provides maximum radiation exposure and minimum treatment times.

In additional embodiments, the light sources can be made into or incorporated in a blanket or other structure which is configured to surround the patient so that all sides of the patient's body are treated simultaneously. The lamps can be spaced on the blanket or interior surface of the structure to facilitate directing the blue LED light at all body surfaces. The structure can be a polygonal, oval or cylindrical chamber or enclosure that is either closed or open at the top. Preferably, the enclosure does not extend above the head of the person to be treated to minimize concerns of eye damage from light exposure. Alternatively, the lamps can be positioned only adjacent the patient's upper torso and legs as shown in other embodiments herein. The wattage and treatment time would be the same as in the other embodiments disclosed herein.

Figure 7:
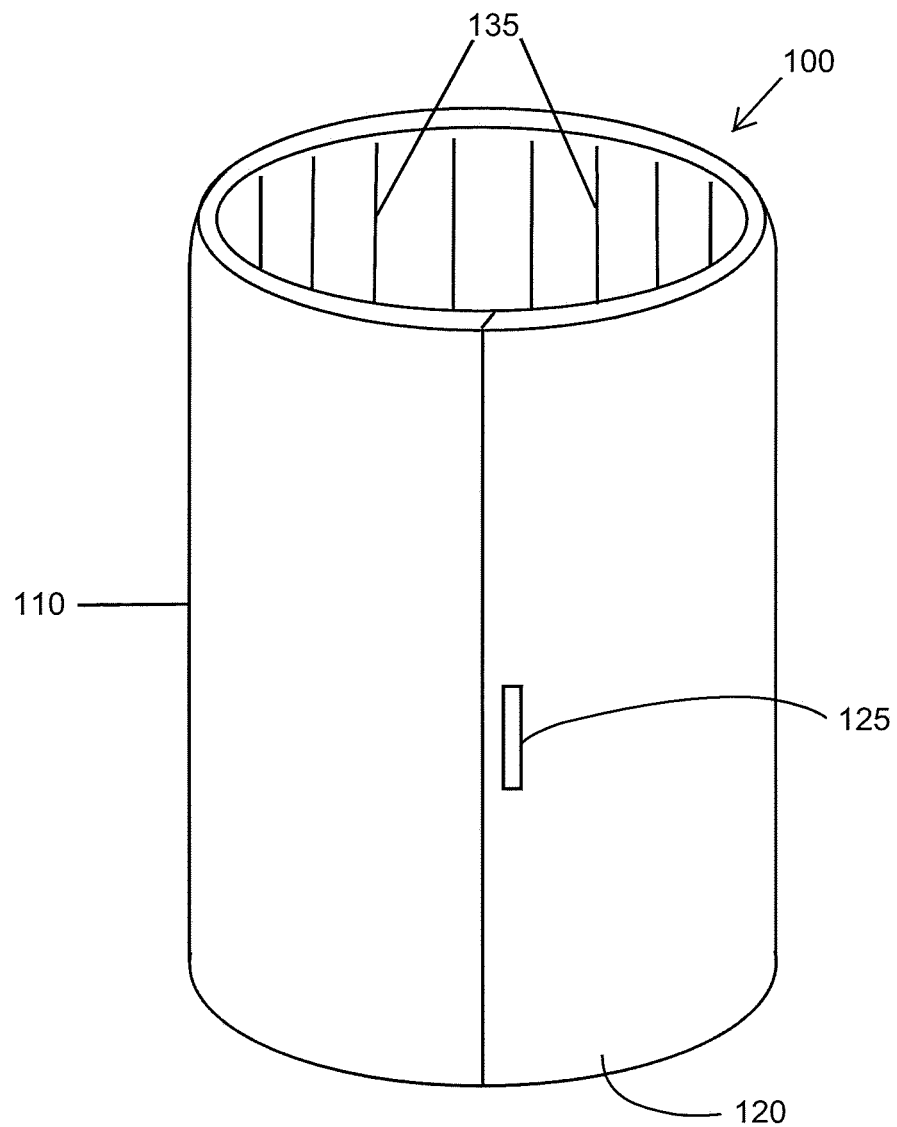
FIG. 7 illustrates a cylindrical chamber for surrounding the patient and directing blue LED light at all skin surfaces.

As shown in FIG. 7, a cylindrical enclosure may be provided. This enclosure can include a door or movable panel that would allow the patient to enter into the enclosure. The LED lamps would be mounted uniformly in spaced locations on the internal surface of the enclosure so that the patient's entire body is illuminated with the blue LED light. In a preferred embodiment, the enclosure is not taller than the height of the person who is being treated. Typically, a height of about 5 feet is acceptable, with a small raised platform being placed inside of the enclosure for shorter people so that their head extends above the top surface of the enclosure. Alternatively, the enclosure can be configured to be raised or lowered to conform to the height of the individual patient to be treated.

The cylindrical enclosure or chamber 100 of FIG. 7 includes a wall member 110 that provides the enclosure, access to which is provided by door 120 which is openable by handle 125. As noted herein, a square rectangular or other polygonal shaped enclosure can also be used. The lamps can be mounted on the interior surface of the chamber so that when illuminated all body surfaces of the patient standing therein would be exposed to the blue LED light radiation.

In some embodiments, the door can instead be a sliding door or a curtain. For these, the door or curtain would not include lamps so the patient would have to change position during the treatment to obtain uniform coverage of the LED light on his or her body.

When a blanket enclosure is used, it can be suspended from hoops or mounted on a structure that provides the blanket in a vertical orientation in a configuration that surrounds the patient.

Figure 6:
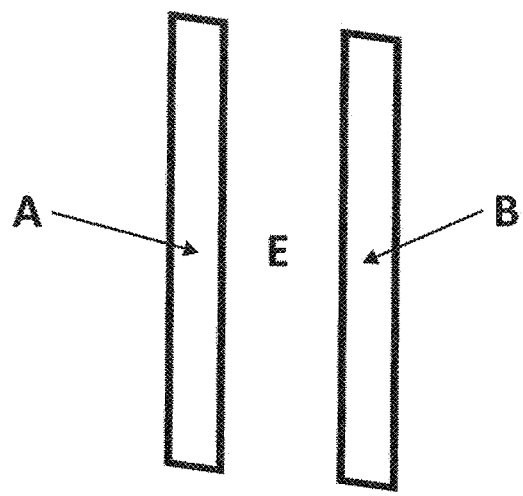
FIG. 6 shows different location points which are identified for radiation measurement. The identified location points (A, B, C, D, E and F) are labeled in relevance to the positions of the LED baton lamps.
Figure 6:
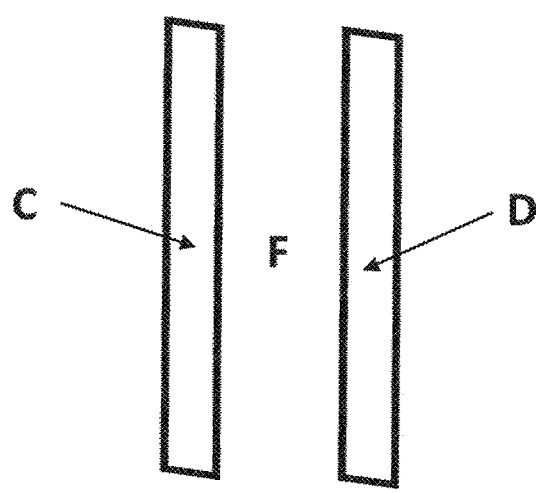

For all embodiments, the exposed skin can be at the distance of about 5.08 cm to 30.48 cm (2 to 12 inches), preferably at the distance of about 10.16 cm (4 inches), or preferably at the distance of 30.48 cm (10 inches) from the LED light source. When the distance from the LED light source is at least 25.4 cm (10 inches), the radiation measurements for different locations (i.e. locations A, B, C, D, E and F as shown in FIG. 6) reach similar levels with equal exposure.

The skin in back and front sides of the body is exposed to the LED light source in equal length of time for each treatment. In one embodiment, the total exposure time for both the front and the back sides of the body is about 15 to 100 minutes, preferably around 25 to 50 minutes (in single or multiple treatment sessions, as the absorbance is cumulative. In the most preferred embodiment, the radiation is provided in the range of about 1200 to 2000 watt minutes at 30 to 50 watts for treatment times of 25 to 50 minutes.

The exposure of the LED light through the photo-therapy device and the method of use thereof of the present invention provides effective treatment of the Grover's disease by delivering sufficient energy in blue light for absorption by the exposed skin surfaces of the subject to improve the condition of the rash. These improvements are obtained without the use of pharmaceutical agents applied by ointments, creams or lotions after the light exposure.

EXAMPLES

The following examples illustrate the benefits and advantages of the present invention.

Example 1. Radiation Measurements

The levels of exposure of radiation of the LED light for different locations at different distances from the LED light source were measured. Blue light radiation was provided with four LED baton lamps. Each lamp had wattage of 35-40 watts and emitted light in wavelength range of from 410 to 490 nm with the center of the spectrum at 450 nm. The baton lights were approximately 2 feet long and attached to a wall arranged as shown in FIG. 6. These lights include a power cord which is liked to a power source that is plugged into a conventional 120 V wall outlet. The power source provides the necessary wattage for the lamps. FIG. 6 also shows different location points which were identified for radiation measurement. Table 1 shows the typical reading at three different distances from the LED light source for six different locations (A, B, C, D, E and F).

When the distance from the LED light source was at least 25.4 cm (10 inches), the radiation measurements for the six different locations (i.e., locations A, B, C, D, E and F) reached similar levels with equal exposure.

Table 1. Radiation measurements in watts per meter squared (W/m$^2$)

TABLE 1

Radiation measurements in watts per meter squared (W/m$^2$)

| Location | Radiation at different distances from light source (W/m$^2$) | | |
|---|---|---|---|
| | 10.16 cm (4 inches) | 15.24 cm (6 inches) | 25.4 cm (10 inches) |
| A | 40 | 31 | 23 |
| B | 52 | 35 | 23 |
| C | 42 | 29 | 22 |
| D | 44 | 36 | 24 |
| E | 29 | 28 | 24 |
| F | 34 | 32 | 23 |
| Average radiation | 40.2 | 31.8 | 23.5 |

Example 2. Blue Light Exposure for Treating Grover's Disease

Blue light radiation was provided with four LED baton lamps. Each lamp had wattage of 35-40 watts and emitted light in wavelength range of from 410 to 490 nm with the center of the spectrum at 450 nm. Each of the LED baton lamp was approximately 2 feet long and attached to a wall in the arrangement shown in FIGS. 1B and 6. The skin of the patient with Grover's disease was exposed to the LED light radiation. Eyes of the patient were protected from the LED lights, such as wearing sunglasses with heavy tint or non-transparent material. The patient stood in front of the LED lights and exposed the skin of the body for both sides, i.e., front and back sides of the body. The exposed skin is at the distance of 25.4 cm (10 inches) from the LED light source. Different exposure times of from 10 to 40 minutes were tested. The skin in back and front sides of the body was exposed to the LED light source in an equal length of time.

The status of the skin was improved after the LED light exposure. The presence of rash was dramatically reduced from one that presented multiple raised red lesions before the treatment to one having only one or two small pink lesions after the LED light exposure. The exposure of the LED light was very effective in the treatment of the skin of the patient with Grover's disease, when sufficient energy reached the skin, preferably at the distance of 25.4 cm (10 inches) for about 22 minutes for each side of the body, i.e. the front and back sides of the body.

In comparison, previous treatments of the subject using conventional pharmaceuticals provided no measurable improvement in skin status.

The term "about" as used herein means that the value is not necessarily precise and could vary by ±10% or preferably by ±5%.

It is to be understood that the present invention is not to be limited to the exact description and embodiments as illustrated and described herein. To those of ordinary skill in the art, one or more variations and modifications will be understood to be contemplated from the present disclosure. Accordingly, all expedient modifications readily attainable by one of ordinary skill in the art from the disclosure set forth herein, or by routine experimentation therefrom, are deemed to be within the true spirit and scope of the invention as defined by the appended claims.

What is claimed is:

1. A method of treating a skin rash on exposed skin surfaces of at least a patient's upper torso which comprises applying blue light radiation so that the patient absorbs blue light radiation from exposure to at least 500 to 2500 watts-minute of such radiation to treat, reduce or eliminate the rash, wherein the radiation is uniformly applied to the exposed skin surfaces by blue LED light generating lamps each having a wattage of at least 5 W and at a total exposure time of 10 to 100 minutes, with the emitted blue light having a wavelength in the range of between 410 and 490 nm, wherein the lamps are spaced at a distance from the patient that is positioned to correspond to a desired absorption or radiation based on a selected treatment time.

2. The method of claim 1, wherein the blue light radiation is applied to both front and back sides of the patient so that the patient absorbs blue light radiation from exposure to at least 1000 watts-minute of such radiation, wherein the radiation is uniformly applied to the exposed skin surfaces by a plurality of blue LED light generating lamps each having a wattage of at least 25 W and at a total exposure time of at least 40 minutes, with the emitted blue light having a wavelength in the range of between 425 and 475 nm.

3. The method of claim 1, wherein the rash is present on a patient suffering from Grover's disease or diseases which are associated or co-existent with Grover's disease.

4. The method of claim 3, wherein the subject to be treated is a male who is 40 years old or older, the lamps have a wattage of at least 30 watts and the radiation is applied at a total treatment time of at least 40 minutes so that the patient absorbs blue light radiation from exposure to at least 1200 watts-minute of the radiation.

5. The method of claim 1, wherein the lamps are arranged about 5.08 cm to 50.8 cm (about 2 to 20 inches) from the patient.

6. The method of claim 5, wherein the lamps are configured and arranged on one or more supporting surfaces to provide a uniform application of the radiation onto exposed skin surfaces of the patient.

7. The method of claim 6, wherein the lamps comprise between 2 and 12 baton lamps oriented longitudinally along the height of the patient with at least two baton lamps aligned with the patient's upper torso and optionally with at least two baton lamps aligned with the patient's legs.

8. The method of claim 7, wherein the one or more supporting surfaces are arranged on a vertical wall or walls to allow the subject to stand adjacent the wall or walls with one side of his or her body facing the lamps for a first period of treatment for that side and then to turn to orient his or her opposite side to face the lamps for a further period of treatment.

9. The method of claim 6, wherein the supporting surface provide a horizontal orientation of the lamps longitudinally above the patient with at least two baton lamps aligned with the patient's upper torso and with at least two baton lamps aligned with the patient's legs.

10. The method of claim 6, wherein the lamps are arranged on internal surfaces of an enclosure that surrounds the patient to be treated.

11. The method of claim 6, wherein the one or more support surface(s) comprise(s) one or more structure(s) associated with and placed above an upper surface of a bed or table.

\* \* \* \* \*